(12) United States Patent
Schmutz et al.

(10) Patent No.: US 6,261,097 B1
(45) Date of Patent: Jul. 17, 2001

(54) RETAINING ELEMENT FOR AN IMPLANT AND AMPOULE FOR PRESERVING SAID IMPLANT

(75) Inventors: Werner Schmutz, Niederdorf (CH); James Percival Simpson, Waldenburg (GB)

(73) Assignee: Institut Straumann AG, Waldenburg (CH)

( * ) Notice: Subject to any disclaimer, the term of this patent is extended or adjusted under 35 U.S.C. 154(b) by 0 days.

(21) Appl. No.: 09/424,896

(22) PCT Filed: May 25, 1998

(86) PCT No.: PCT/CH98/00218

§ 371 Date: Feb. 22, 2000

§ 102(e) Date: Feb. 22, 2000

(87) PCT Pub. No.: WO98/55039

PCT Pub. Date: Dec. 10, 1998

(30) Foreign Application Priority Data

Jun. 2, 1997 (CH) .................................................. 1314/97

(51) Int. Cl.$^7$ .................................................. A61C 8/00
(52) U.S. Cl. ........................................ 433/173; 433/201.1
(58) Field of Search .................................... 433/172, 173, 433/174, 201.1

(56) References Cited

U.S. PATENT DOCUMENTS

| 4,856,648 | 8/1989 | Krueger . | |
|---|---|---|---|
| 5,062,800 | * 11/1991 | Niznick | ................................ 433/229 |
| 5,312,254 | 5/1994 | Rosenlicht . | |
| 5,368,160 | * 11/1994 | Leuschen et al. | ............... 433/174 X |
| 5,538,428 | * 7/1996 | Staubli | ................................ 433/173 |

FOREIGN PATENT DOCUMENTS

| 0231730 | 10/1990 | (EP) . |
| 9110410 | 7/1991 | (WO) . |
| 9619947 | 7/1996 | (WO) . |

OTHER PUBLICATIONS

Oral Implantology by Schroeder/Sutter/Buser/Krekeler, George Thieme Verlag Stuttgart and New York, 2nd Edn., 1996, pp 124–143 and 219–221.

* cited by examiner

Primary Examiner—Nicholas D. Lucchesi
(74) Attorney, Agent, or Firm—Selitto, Behr & Kim

(57) ABSTRACT

The proposal is for a holding element (100) which can be screwed into the internally threaded bore (14) of the implant (1) even during production of the latter and can thus be used to grip or hold the implant for the following production phases. Furthermore, the holding element (100) serves to fix an implant (1), which is screwed thereto, inside an ampoule (200) and for the application of a screwing-in tool for implantation. The particular feature of the ampoule (200) lies in the fact that it has a large-area, lateral cutout (231) in the casing and also a fixing part (210) for accommodating the holding element (100) in a clamped manner. The implant (1) can thus be pulled laterally out of the ampoule (200). The devices facilitate handling of the implant (1) during production and insertion into the bone.

13 Claims, 8 Drawing Sheets

Figure 1A:
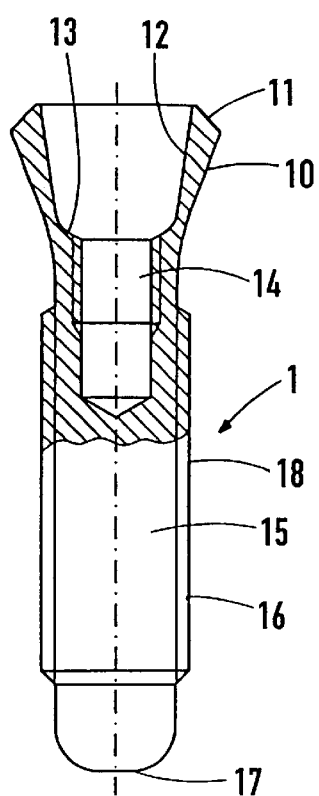

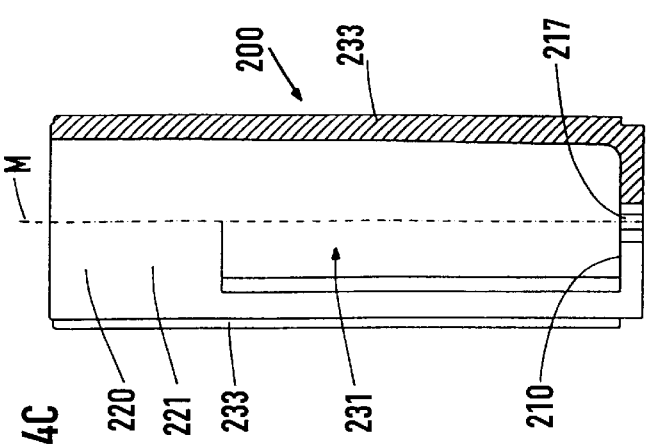
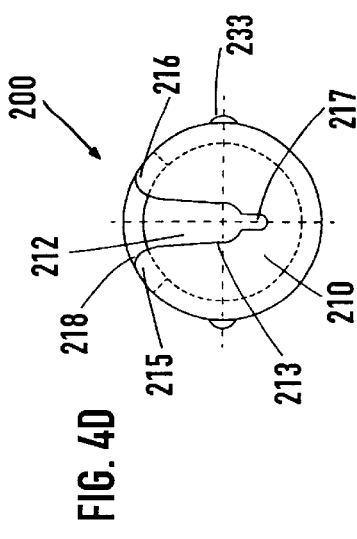
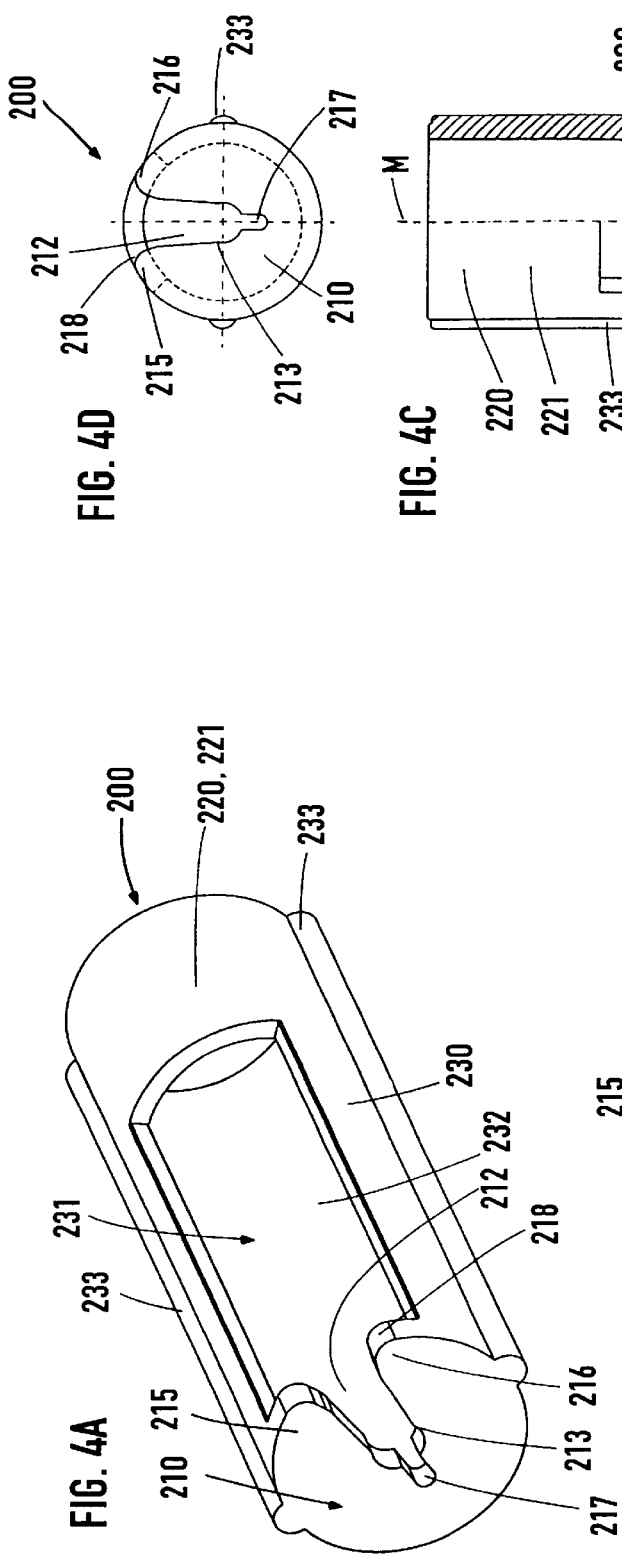

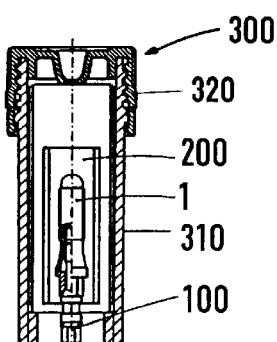
FIG. 8A
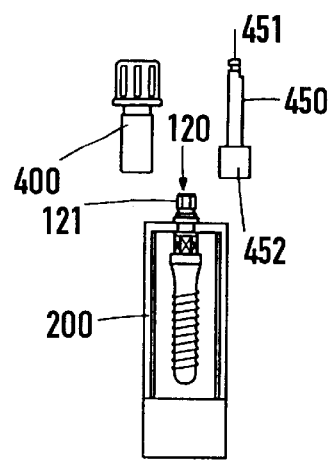
FIG. 8D
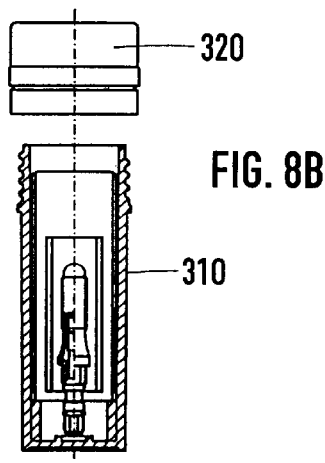
FIG. 8B
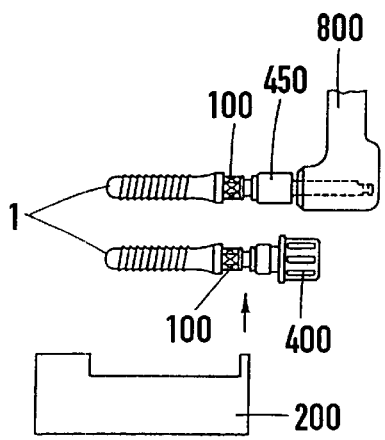
FIG. 8E
FIG. 8C
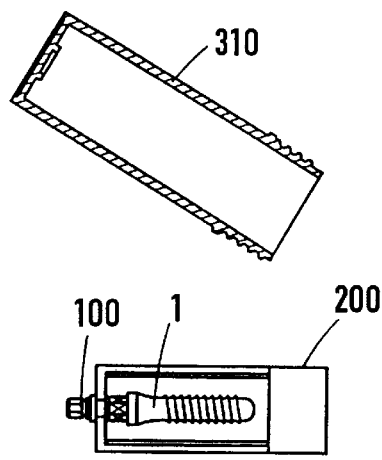
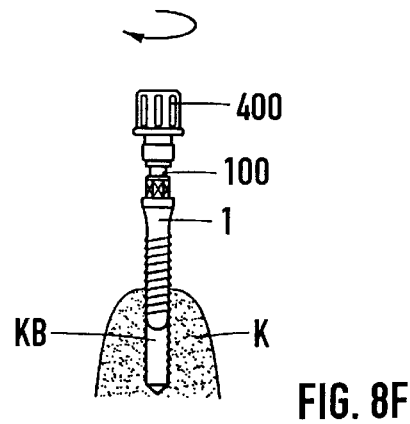
FIG. 8F

RETAINING ELEMENT FOR AN IMPLANT AND AMPOULE FOR PRESERVING SAID IMPLANT

APPLICATION AREA OF THE INVENTION

The present invention relates to a holding element for an implant, primarily in screw or cylinder form. A first type of implant which may be considered has a bore which at least in principle emerges axially on the implant head and has an internally threaded section. The mouth of the bore is surrounded by an implant shoulder, which forms the upper end of the implant. The second type of implant which is suitable has a segment which projects above the implant shoulder and has an internally threaded section. The segment has a predominantly polygonal or conical outer contour. Such implants are used, for example, in the dental sector or in bone surgery. The implant is intended to be inserted—i.e. screwed or pressed—into a receiving bore which has been prepared in the bone. This depends on whether the receiving bore has an internal screw thread or the implant has a self-tapping thread or the implant has no thread at all. Furthermore, the invention relates to an ampoule in which the implant is stored.

The holding element can be employed during a number of production phases of the implants in order to prepare them prior to the surgical intervention, and can also be employed directly during implantation. The primary application area of the invention is where the implants, for example for reasons of the sterile operating procedure required, must not be taken hold of at least directly with the hands, and where it is important to hold the implants secure.

The holding element can also be used inside a special ampoule which serves to transport and store the implant. During the surgical intervention, the implant can be removed from the ampoule under sterile conditions using an attached tool and then, by means of this tool, can be inserted into the receiving bore in the bone. To ensure a sterile operating procedure, the ampoule is stored in a secondary capsule until the start of the intervention.

PRIOR ART

The first type of implant mentioned is described, for example, in the monograph by SCHROEDER/SUTTER/BUSER/KREKELER: Oral Implantology, Georg Thieme Verlag Stuttgart and New York, 2nd Edn., 1996, pp 124–143, and in WO-A-96 19947. The second type of implant, having the outer segment which projects above the implant shoulder, is shown, for example, in WO-A-91 10410 and U.S. Pat. No. 5,538,428. Various manipulation members are used for handling these implants, the implants being taken hold of in a positively and/or non-positively locking manner.

The following situation exists with regard to ampoules where sterile conditions are to be maintained: in principle, the ampoules can also be divided into two types. In a first type, the implant stored in the ampoule is connected to the cover, which directly or indirectly functions at the same time as a screwing-in tool and is used at least to some extent to screw in the implant. According to U.S. Pat. No. 4,856,648, in its most simple form the cover has an extension with a non-rotationally symmetrical engagement contour which interacts with a complementary contour on the implant head. It is known from U.S. Pat. Nos. 5, 312,254 and 5,538,428 to introduce a connecting element between the cover and the implant, which connecting element transmits the rotational screwing movement. U.S. Pat. No. 5,062,800 has disclosed an ampoule where the cover represents the connecting element for the screwing-in tool. These ampoules are to some extent very expensive, as the tool components are generally only used once. Furthermore, handling these ampoules often requires a relatively large number of operations, and in addition external screwing-in tools are also required. Finally, it is doubtful whether the implants are gripped sufficiently reliably by the screw covers or the connecting elements.

In the case of the second type, the implant arranged in the ampoule has to be taken hold of and screwed in using an external tool. The present invention relates to this type of ampoule. EP-B-0 231 730 discloses a simple variant where the implant is positioned in a sleeve and the implant head projects above and closes off one end of the sleeve. The sleeve is fused into a glass ampoule, which has constrictions and an internal spring. The implant head is supported against the spring, and the sleeve is fixed inside the constrictions, one constriction at least partially closing off the bottom of the sleeve. Suitable external tools are used to grip the implant, while on the ampoule itself there are no means whatsoever which facilitate and make more reliable the removal of the implant from the ampoule and transportation to the site of implantation.

Such a type of ampoule with sterile conditions is also disclosed by SCHROEDER/SUTTER/BUSER/KREKELER, loc. cit., pp. 219–221. The capsule-like ampoule has a removable cover and a partition which extends perpendicular to the longitudinal axis, close to the cover. In this partition, there is an axial passage in which a bearing ring rests, in which the head of the implant is positioned, while the apical part of the implant projects into the ampoule. In order to take hold of the implant, a lockable screwing-in tool is attached, the threaded mandrel of which is screwed into the axial threaded bore, which is in the form of a blind bore and is present in the implant head. Having been screwed onto the screwing-in tool, the implant is then removed from the ampoule. The implant is then positioned in the hole in the bone, spanners being attached to the screwing-in tool. Finally, the lock between the implant and the screwing-in tool has to be released again, so that the screwing-in tool can be unscrewed. This handling method requires numerous operations, a plurality of instruments and particular care and skill on the part of the surgeon. The instruments attached while the implants are being introduced into the bone are unsuitable as manipulating members during the overall production process of the implants; separate holders have to be used for this purpose.

OBJECT OF THE INVENTION

In view of the abovementioned drawbacks of the devices which have been used to date to grip and hold implants of the two types mentioned above, the problem underlying the invention is that of perfecting such devices. It is desired to make the connection between the implant and the holding element more efficient in production terms, more widely usable, reliable and also, ultimately, able to be released without problems. In the preparatory phase of the surgical intervention and also during the intervention, it is necessary to ensure that the implants used can always be guided reliably, can in no way become loose and uncontrollable and that the sterility requirements are fulfilled. The holding element should significantly facilitate removal of the implant from the ampoule using the attached screwing-in tool and insertion of the implant into the bone. With regard to the ampoule, the object is to develop it further in such a manner that the implant is held reliably therein and can be removed in an uncomplicated manner and under sterile conditions using a screwing-in tool which is simple to attach. If the implant is removed from the ampoule correctly, it is intended that the risk of contact between implant and ampoule should in principle be ruled out, so as to avoid contamination or damage to the intra-ossal implant surface. It is to be envisaged that the ampoule can be inserted into a conventional external capsule for storage and transportation. Moreover, it should be possible to produce the ampoule as a disposable item in a material-saving and, overall, cost-effective manner.

OVERVIEW OF THE INVENTION

The holding element comprises a sleeve part and a rotatable screw which projects through the sleeve part and can move axially to a limited extent. The sleeve part has, at the bottom, a cylindrical shoulder part which ends with a mating shoulder which is directed downwards and is complementary to the implant shoulder. An upwardly directed external polygon segment extends above the shoulder part. An axial bore allowing the passage of the shaft of the screw runs through the sleeve part. In an advantageous refinement, the axial bore has an internally threaded section.

The screw comprises the lower screw shank, the adjacent fixing part and the upper extension, preferably with an external polygon. The screw shaft is divided up into the externally threaded part, which is present at the free end, and the attached cylindrical part. Between a first and a second cylindrical collar, the fixing part has an annular groove. If sleeve part and screw have been assembled to form the holding element, then the externally threaded part of the screw shank has firstly been screwed through the internally threaded section so that the externally threaded part projects above the mating shoulder of the sleeve part and the cylindrical part of the screw shaft then lies inside the internally threaded section. Having been assembled in this way, the sleeve part is axially displaceable between externally threaded part and the first collar which faces the latter.

When the holding element has been screwed onto an implant, the mating shoulder of the sleeve part rests in a complementary manner on the implant shoulder and the first collar rests on the external polygon segment. The externally threaded part of the screw shaft engages in the internally threaded bore in the implant head.

The external polygon of the extension of the screw serves primarily to grip the holding element, which is connected to the implant head, by means of a screwing-in tool, in order to remove the implant from the ampoule without direct contact, to transfer it to the site of use and to implant it there. The annular groove on the fixing part of the screw is intended in particular to latch into engagement with a fixing part on the ampoule, in order to retain the implant which is supported by the holding element in a releasable and suspended manner inside an ampoule. The external polygonal segment of the sleeve part is primarily provided for the attachment of an unscrewing spanner when unlocking the holding element which has been screwed to the implant.

If the holding element is attached to the implant head as early as during production of the implant, the holding element offers the option of attaching manipulating members thereto for further processing of the implant. This facilitates handling of the implants even during their production.

In the widest ranging application and configuration, the holding element is connected to the implant as early as during the production of the latter, so that the following functions then emerge overall:

a) gripping and holding of the implant for the following production phases; and
b) retaining of the implant inside an ampoule; and
c) attachment of a screwing-in tool for implanting the implant into the bone.

If the insertion of the implant into the bone per se has finished, the screwing-in tool used can be pulled off the extension. The sleeve part which is resting fixedly on the implant shoulder is unlocked by means of an unscrewing spanner, and then the screw is screwed out of the internally threaded bore in the implant head, so that the holding element is detached from the implant.

The design features of the ampoule, which in principle is cylindrical, consist in the fact that it is open to the sides and has a fixing part in which the implant is held directly or indirectly. When removing the implant from the ampoule, it is pulled out laterally. In an advantageous version, the fixing part clamps in a holding element which is connected to the implant head, so that the implant is supported by the holding element and does not come into contact with the wall of the ampoule. A screwing-in tool or an adapter for a screwing-in tool can be attached directly to a free extension of the holding element, by means of which screwing-in tool or adapter the implant can be removed from the ampoule without contact. The ampoule can be inserted into a conventional external capsule.

The holding element of the invention simplifies handling of the generic implants during production and implantation itself. An implant can be taken hold of on the holding element and manipulating members and screwing-in tools can be attached without problems and released again. In combination with the holding element, the effect is achieved that the ampoule does not have to consist of the same material as the implant or contain a specifically protective insert made of the implant material. The risks of contamination or damage to the implant surface are considerably reduced as a result of the form of the ampoule according to the invention and the nature of suspension of the implant inside the ampoule by means of the holding element. Furthermore, when the ampoule is tipped out of the outer capsule, it quickly comes to a halt on a sterile surface on the operating table and no longer has a tendency to roll off, owing to the centre of gravity lying outside the longitudinal axis. Finally, the ampoule, together with the implant, can be laid down stably, owing to the stand part situated opposite the fixing part, so that attachment of the tools is facilitated.

BRIEF DESCRIPTION OF THE APPENDED DRAWINGS

Figure 1B:
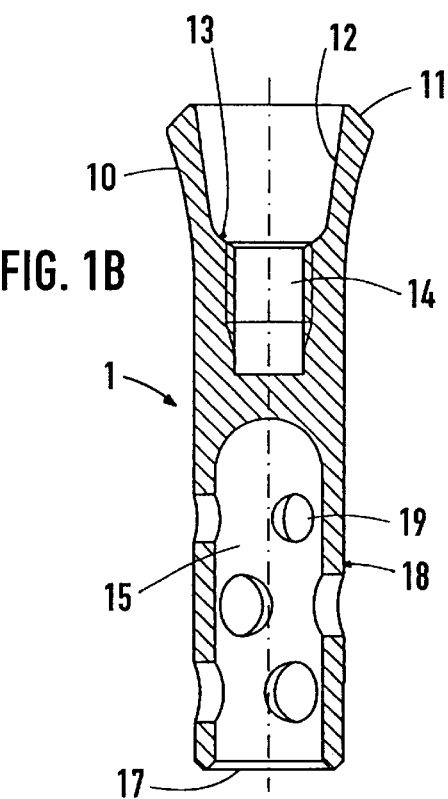
Figure 1C:
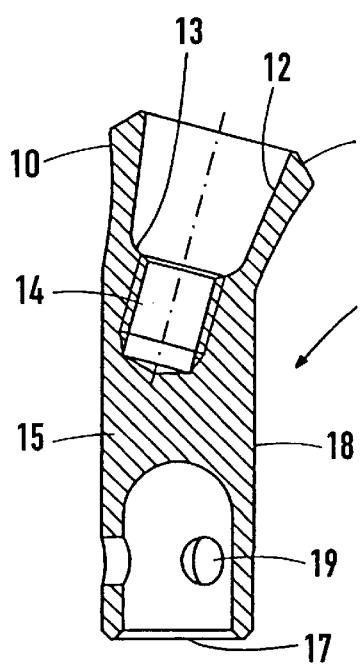
Figure 1D:
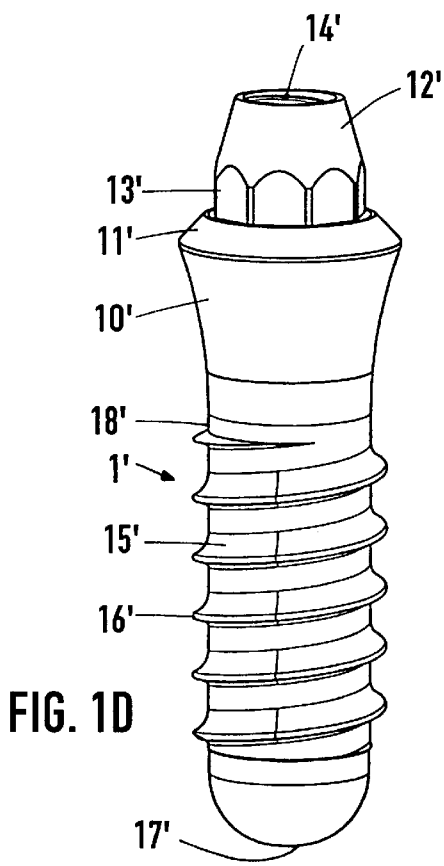
Figure 2A:
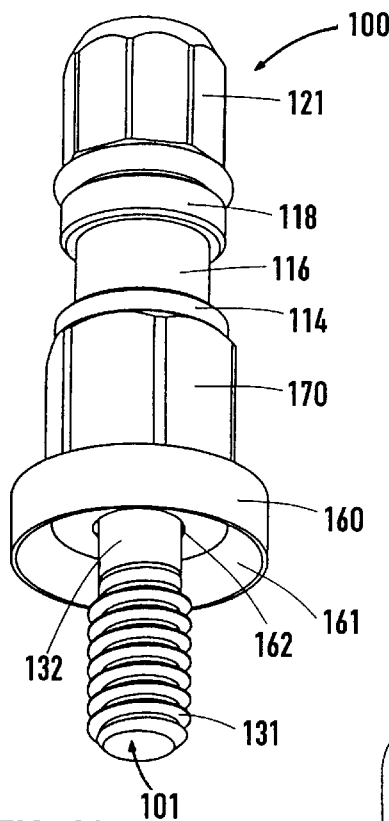
Figure 2B:
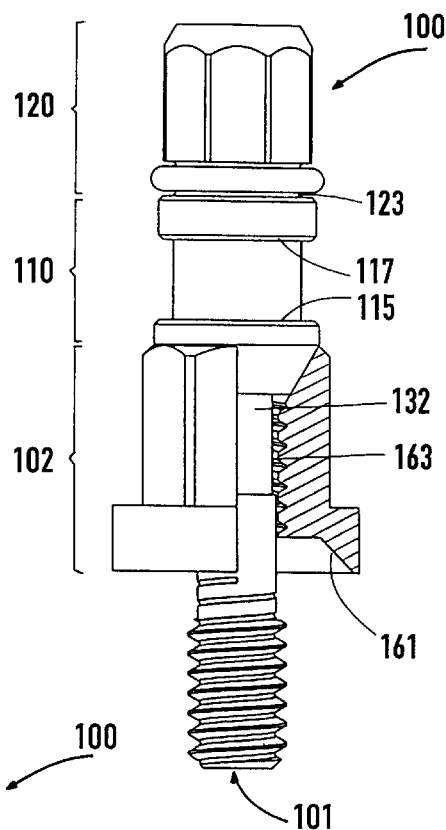
Figure 2C:
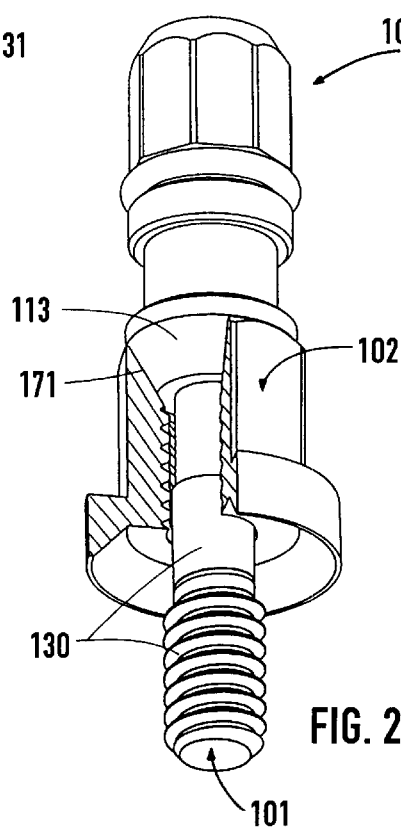
Figure 3A:
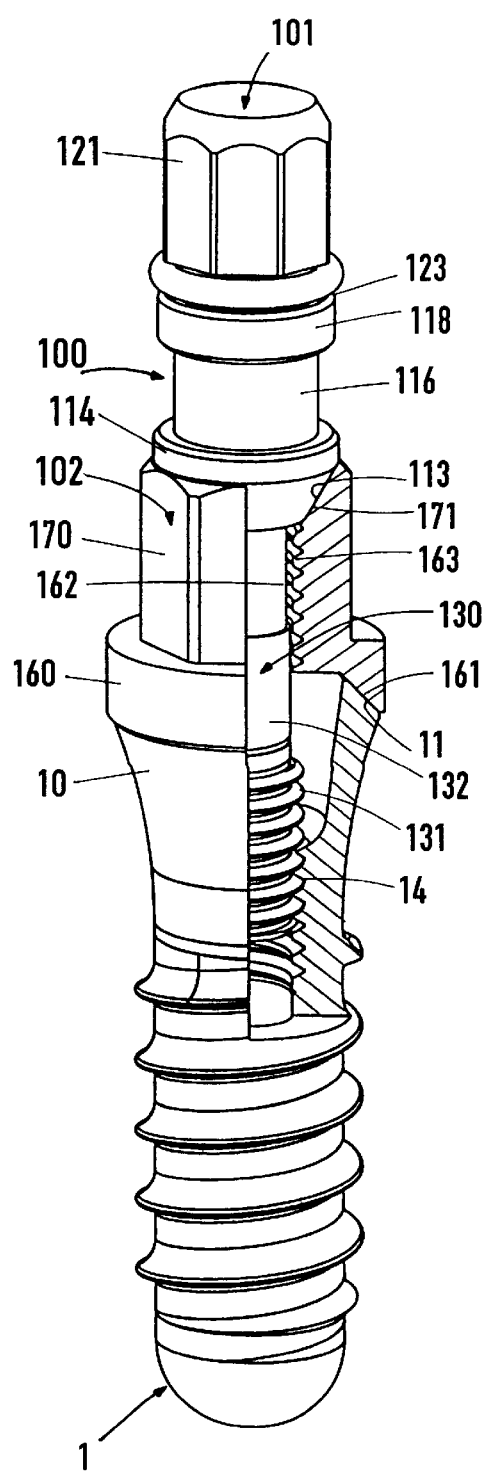
Figure 3B:
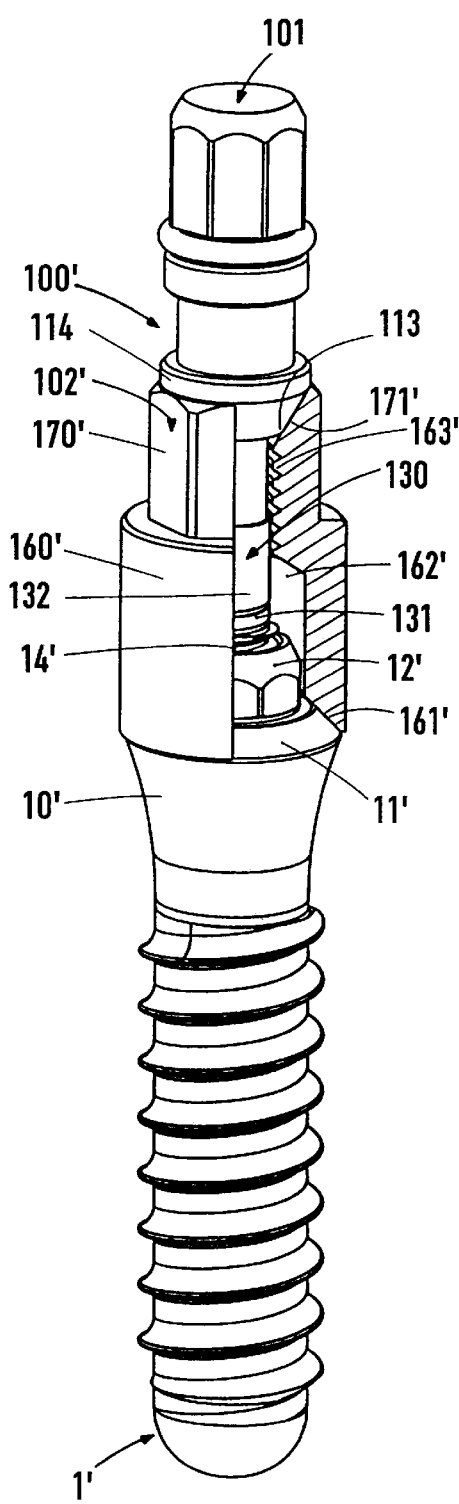
Figure 5:
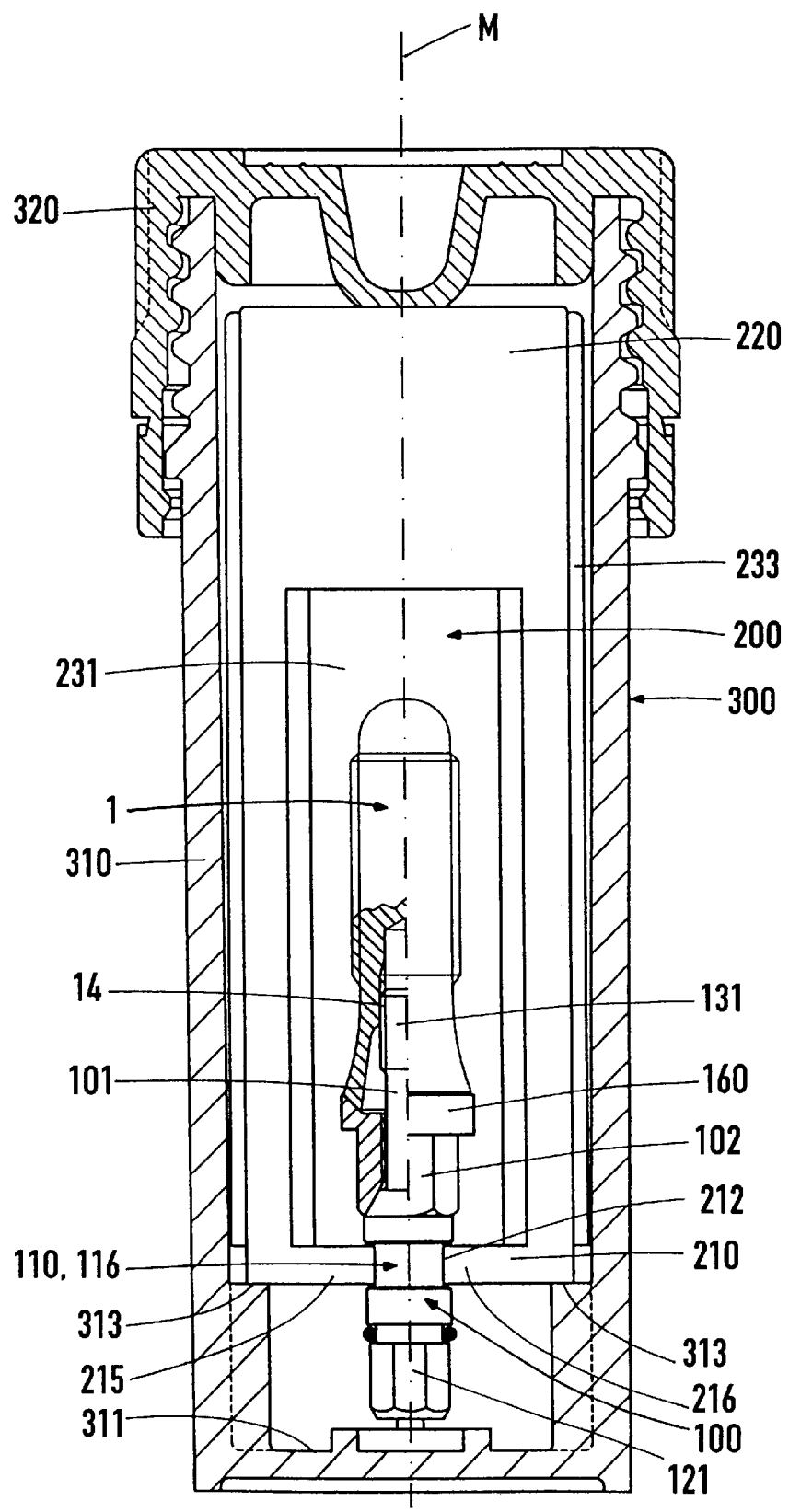
Figure 7:
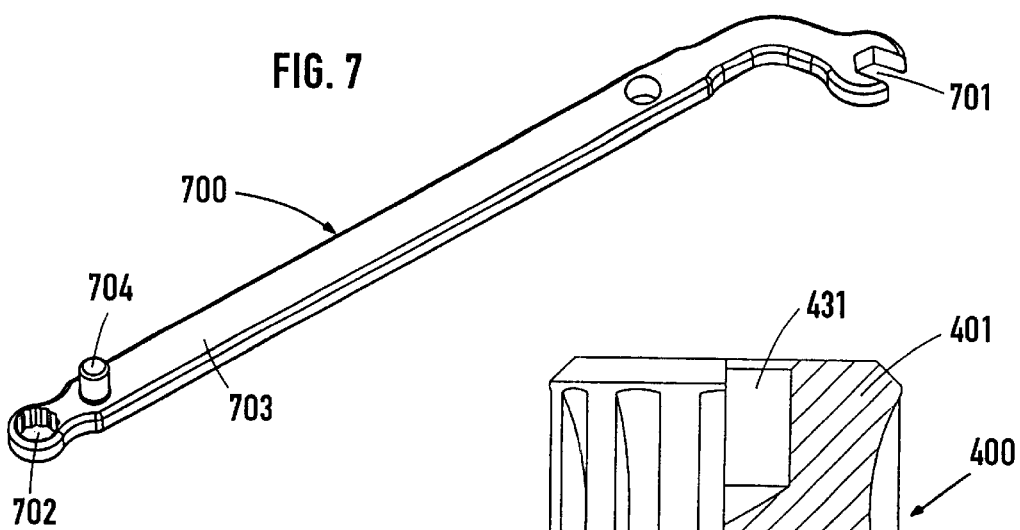
Figure 6B:
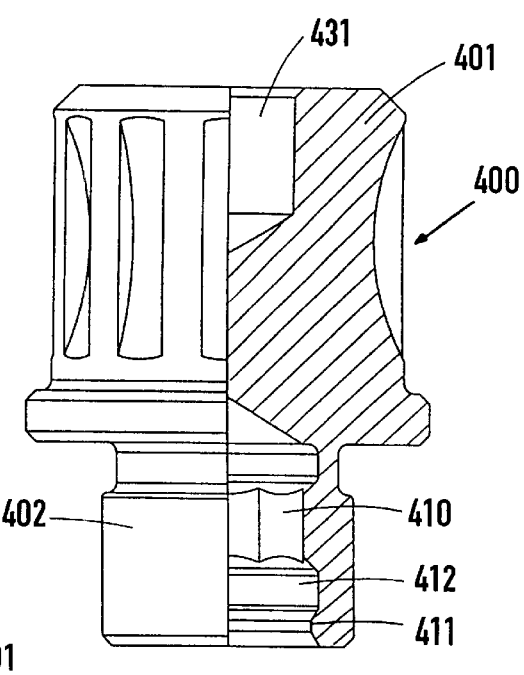
Figure 6A:
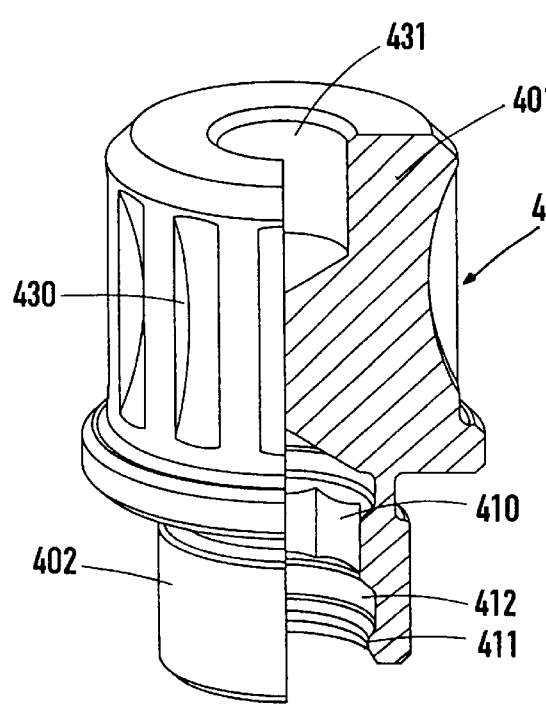
Figure 8G:
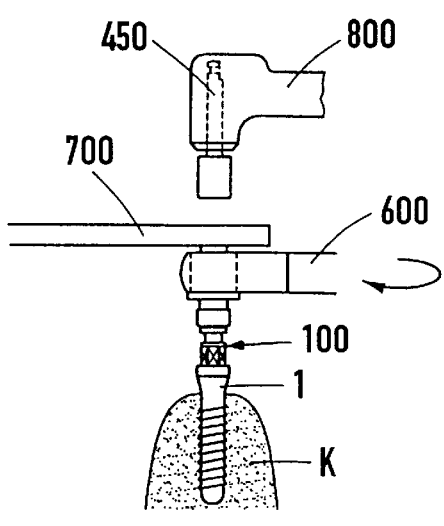
Figure 8I:
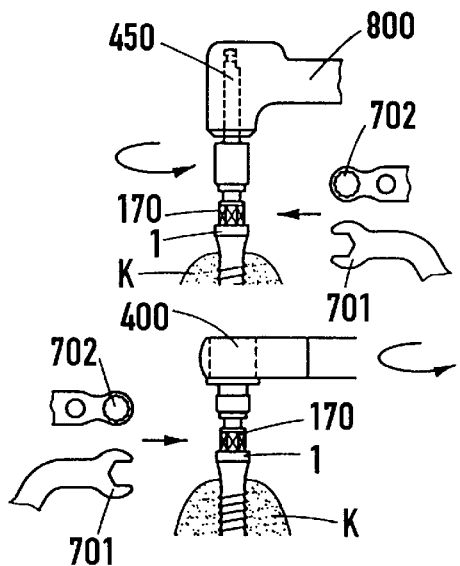
Figure 8H:
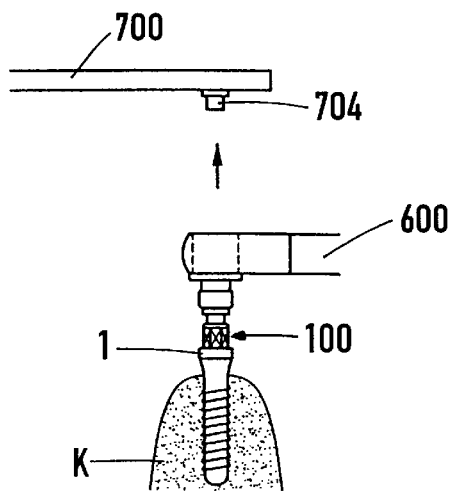
Figure 8J:
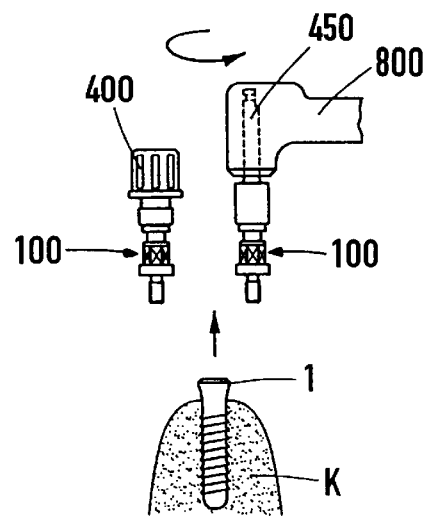

With reference to the appended drawings, there now follows a detailed description of in each case one exemplary embodiment of the holding element according to the invention for the two types of implant and of the ampoule for storing the implant. Finally, possible modifications are mentioned. In the figures:

FIG. 1A—shows a sectional illustration of the first type of a generic implant in the form of a solid screw;

FIG. 1B—shows a sectional illustration of the first type of a generic implant in the form of a hollow cylinder;

FIG. 1C—shows a sectional illustration of the first type of a generic implant in the form of a hollow cylinder with an angled-off implant head;

FIG. 1D—shows the second type of a generic implant in the form of a solid screw, as a perspective illustration;

FIG. 2A—shows a perspective view of a holding element according to the invention having a sleeve part in a first version for the first type of implants in accordance with FIGS. 1A to 1C;

FIG. 2B—shows a front view, partially in section, of the holding element in accordance with FIG. 2A;

FIG. 2C—shows a perspective view, partially in section, of the holding element in accordance with FIG. 2A;

FIG. 3A—shows a perspective view, partially in section, of the holding element in accordance with FIG. 2A, connected to an implant in accordance with FIG. 1A;

FIG. 3B—shows a perspective view, partially in section, of the holding element having a sleeve part in a second version, connected to the second type of implants in accordance with FIG. 1D;

FIG. 4A—shows an ampoule according to the invention, in perspective view onto the outside of the fixing part;

FIG. 4B—shows the ampoule in accordance with FIG. 4A, in perspective view onto the inside of the fixing part;

FIG. 4C—shows a front view, partially in section, of the ampoule in accordance with FIG. 4A;

FIG. 4D—shows the ampoule in accordance with FIG. 4A, in plan view onto the outside of the fixing part;

FIG. 5—shows the ampoule in accordance with FIG. 4A, with a holding element with a sleeve part in a first version in accordance with FIG. 2A and an implant of the first type in accordance with FIG. 1A, surrounded by an external capsule, in longitudinal section;

FIG. 6A—shows a perspective view, partially in section, of a ratchet adapter which is known per se;

FIG. 6B—shows a front view, partially in section, of the ratchet adapter in accordance with FIG. 6A;

FIG. 7—shows a perspective view of an unscrewing spanner which is known per se;

FIGS. 8A to 8J—show the principal handling operations for the ampoule situated in an external capsule in accordance with FIG. 5, with an implant of the first type in accordance with FIG. 1A and a holding element in accordance with FIG. 2A as far as insertion of the implant into the bone;

FIG. 8A—step 1—shows the initial situation; ampoule with implant retained by the holding element, surrounded by a closed external capsule, in longitudinal section in accordance with FIG. 5;

FIG. 8B—step 2—opening of the external capsule by removing the closure cover;

FIG. 8C—step 3—tipping the ampoule out of the external capsule;

FIG. 8D—step 4—preparation of the particular adapter for the alternative screwing-in tools to be attached to the holding element;

FIG. 8E—step 5—removal of the implant with, attached to the holding element, either a ratchet adapter or a motor-driven, dental angle handpiece;

FIG. 8F—step 6—shows the ratchet adapter attached as an alternative to the holding element and insertion of the implant into the bone;

FIG. 8G—step 7—shows the screwing of the implant into the bone, alternatively by means of ratchet and guide spanner or by means of angle handpiece;

FIG. 8H—step 8—shows removal of the guide spanner from the ratchet adapter after the screwing-in of the implant has been completed;

FIG. 8I—step 9—shows the approach of the unscrewing spanner in accordance with FIG. 7 towards the holding element for the purpose of unlocking; and FIG. 8J—step 10—shows the removal of the unscrewed holding element from the implant head.

EXEMPLARY EMBODIMENTS

The following statement applies to the whole of the rest of the description. If, for the sake of clarity of the drawing, a figure contains reference numerals which are not explained in the immediately associated text of the description, reference is made to where they are mentioned in previous descriptions of figures; for the sake of clarity, repeated designation of components in following figures is generally dispensed with, as long as it can be clearly seen from the drawings that these are "recurring" components.

FIG. 1A

The implant 1 of the first type in this figure is in the form of a solid screw and, at the top, has the implant head 10 which is widened in the form of a trumpet and at the top ends with the conical implant shoulder 11. The implant shoulder 11 surrounds a conical bore 12 which opens out here, widens outwards and as a threaded bore 14 continues further downwards beneath the base of the bore 13. Towards the apical end, the root part 15, which has the external screw thread 16, ends with the implant tip 17 and is intended to be inserted into the bone, extends beneath the implant head 10. The threaded bore 14 serves to accommodate the threaded part of an abutment (not shown), while the conical bore 12 accommodates the conical nose of the abutment. The implant 1 usually consists of titanium and on the outside has an implant casing 18 with a special surface structure promoting bone integration.

FIGS. 1B and 1C

The implant in accordance with FIG. 1B is a hollow cylinder, the root part 15 of which is hollow and, in the implant casing 18, has a plurality of continuous, peripheral bone-integration holes 19, which allow the regenerating bone to grow through them, leading to fixed anchorage in the bone. The hollow cylinder does not have an external screw thread, but also has the special surface structure on the outside of the implant casing 18. The implant 1 in accordance with FIG. 1C differs from the hollow cylinder shown in FIG. 1B only by the fact that the implant head 10 is angled off with respect to the root part 15.

FIG. 1D

This single-piece implant 1' of the second type in this case is in the form, for example, of a solid screw and differs from the configuration in accordance with FIG. 1A only with regard to the condition of the implant head 10'. In the second type, the conical bore 12, the bore base 13 and the threaded bore 14 are absent. However, analogously to the first type, the implant shoulder 11', the root part 15', the external screw thread 16', the implant tip 17' and the implant casing 18' are present. Instead of the internal configuration with the conical bore 12, the second implant type 1' has a male segment 12' which projects above the implant shoulder 11', emerges axially and centrally from the implant 1' and tapers conically in the direction away from the implant 1'. A non-rotationally symmetrical contour 13' in the form of an external polygon, is present on the segment 12' for the purpose of positioning further attachments. Preferably, the non-rotationally symmetrical contour 13' is situated at the transition to the implant shoulder 11'. For further implant additions, the segment 12' has an axial threaded bore 14'.

FIGS. 2A to 2C

The holding element 100 depicted is provided for the first implant type 1 having the conical bore 12. A sleeve part 102 and a rotatable screw 101, which projects through the sleeve part 102 and is axially movable to a limited extent, form the two constituents of the holding element 100. At the bottom, the sleeve part 102 has a cylindrical shoulder part 160, which ends with a downwardly directed mating shoulder 161 which is complementary to the implant shoulder 11. An external polygonal segment 170 extends axially upwards from the shoulder part 160. An axial bore 162 with an internally threaded section 163 allowing the passage of the shaft 130 of the screw 101 runs through the sleeve part 102.

The screw shaft 130 is adjoined by a fixing part 110, and the latter is adjoined in turn by the extension 120, which ends at the top and has an external polygon 121. The screw shaft 130 is divided into the externally threaded part 131, which is present at the free end, and the attached cylindrical part 132. The fixing part 110 has a first cylindrical collar 114 and a second cylindrical collar 118, between which there lies a cylindrical section 116 of reduced diameter. The collars 114, 118 are widened with respect to the diameter of the screw shaft 130. At the transition between the cylindrical part 132 and the first collar 114, a conical shoulder 113 is formed, which is intended to bear axially, in the form of a circle and in a positively locking manner against the upper conical support shoulder 171 on the external polygonal segment 170. Annular shoulders 115,117 are produced at each of the transitions between the cylindrical section 116 and the first and second collars 114,118. The cylindrical section 116, together with the two adjoining annular shoulders 115,117, forms the fixing part 110 of the holding element 100. The peg-like extension 120 has the external polygon 121 as its non-rotationally symmetrical contour, onto which a tool, e.g. a screwing-in tool, can be attached. To impede the plug connection between the external polygon 121 and the adapted tool, a radial groove 123 is present on the extension 120, between the second collar 118 and the external polygonal segment 170, in order to arrange a securing element—preferably an O-ring—therein.

In order to assemble the sleeve part 102 and screw 101 to form the holding element 100, the externally threaded part 131 of the screw shaft 130 has to be screwed through the internally threaded section 163, so that the externally threaded part 131 projects beyond the mating shoulder 161 of the sleeve part 102 and the cylindrical part 132 of the screw shaft 130 then lies inside the internally threaded section 163. Having been assembled in this way, the sleeve part 102 is axially displaceable between externally threaded part 131 and the first collar 114 which faces the latter.
FIG. 3A When the holding element 100 has been screwed onto an implant 1—in this case an implant 1 of the first type and hence a corresponding holding element 100 in the first version, —the mating shoulder 161 of the shoulder part 160 of the sleeve part 102 fits on the implant shoulder 11 and the conical shoulder 113 of the first collar 114 rests on the support shoulder 171 of the external polygonal segment 170. The externally threaded part 131 of the screw shaft 130 of the screw 101 engages in the internally threaded bore 14 in the implant head 10 and the unthreaded cylindrical part 132 of the screw shaft 130 penetrates through the internally threaded section 163 inside the sleeve part 102.
FIG. 3B In this figure, an implant 1' of the second type—having a male segment 12' projecting above the implant shoulder 11'—is connected to an associated holding element 100' of the second version. In order to accommodate the segment 12' inside the shoulder part 160', the latter is elevated by comparison with the first version and the axial bore 162', which passes through the sleeve part 102', is widened in the region of the shoulder part 160'. Otherwise, this arrangement is analogous to that in accordance with FIG. 3A; thus the mating shoulder 161' of the shoulder part 160' of the sleeve part 102' again fits on the implant shoulder 11' and the conical shoulder 113 of the first collar 114 rests on the support shoulder 171' of the external polygonal segment 170'. The externally threaded part 131 of the screw shaft 130 of the screw 101 is in engagement with the internally threaded bore 14', which extends from the segment 12' into the implant head 10'. The unthreaded cylindrical part 132 of the screw shaft 130 penetrates through the internally threaded section 163' inside the sleeve part 102'.

Advantageously, the holding element 100,100' is connected to the implant 1,1' as early as during production of the latter, so that the holding element 100,100' even during the following production phases offers the option of attaching manipulation members to it or of being used as a support when positioning the implants in devices. The extension 120 and the fixing part 110 are suitable for the attachment of manipulation members. Since the sleeve part 102,102' is placed upon the implant 1,1', the two preferably consist of the same material, e.g. titanium, while, for example, stainless steel is recommended as the material for the screw 101.
FIGS. 4A to 4D The ampoule 200, which is in principle cylindrical, for accommodating an implant 1,1' has a fixing part 210 on the first planar base side and a stand part 220 on the opposite, second planar base side. The cylindrical casing 230 extends between the fixing part 210 and the stand part 220, in which casing there is a large-area cutout 231 which runs from the fixing part 210 as far as the stand part 220 and extends, for example, over a quarter to a half of the radial circumference of the ampoule 200. The implant 1,1' which is held in the ampoule 200 can be pulled out through this lateral cutout 231. Thus the cylindrical casing 230 which remains in the region of the cutout 231 is in the form of an open shell 232, while in the stand part 220 the cylindrical casing 230 is entirely retained, where it produces, as it were, a tubular section 221. The second planar base side is preferably open.

The cutout 231 extends as far as the fixing part 210, which is in the form of a circular end plate, so that the associated first planar base side is largely closed and the cylindrical casing 230 is perpendicular to the fixing part 210. A laterally open indent 212 is situated in the fixing part 210, this indent 212, together with the cutout 231, facing in the same direction. The indent 212 is in principle in the form of a slot with rounded sections 218 at the peripheral entry. In the region of the theoretical centre axis M the indent 212 has a constriction 213, behind which the indent 212 widens in the manner of a semicircle. The result is two mutually opposite jaws 215,216 on the fixing part 210. Beyond the indent 212, cutting further into the fixing part 210 towards the cylindrical casing 230, there is an expansion groove 217, so that when an implant 1,1' or a holding element 100,100' bearing the implant 1,1' is being pressed in and out between the jaws 215,216, the latter are better able to spread apart elastically. When the holding element 100,100' is being pressed in, after its cross-section has overcome the constriction 213, the holding element 100,100' latches into the indent 212 and the jaws 215,216 move closer together again.

Owing to the asymmetric distribution of material, the centre of gravity of the ampoule 200 lies outside the centre axis M, so that an ampoule 200 which is lying horizontally and hence rolling to and fro quickly comes to a halt. In order additionally to prevent the ampoule 200 from rolling off the surface, in each case one bead 233 is provided on the outside of the cylindrical casing 230, in an axial position and parallel to the edges of the cutout 231. The plane which extends between the two beads 233 divides the tubular ampoule 200 into two longitudinal halves. With the stand part 220 at the bottom, the ampoule 200 can be placed vertically resting on the second planar base side. A suitable material for the ampoule 200 is a biocompatible plastic.

FIG. 5

This Figure is described with reference to the implant 1 and the holding element 100. Analogously, it would also be possible to use the implant 1' of the second type in conjunction with a holding element 100' of the second version.

In the finished state, the ampoule 200, with the implant 1 held therein by the holding element 100, is inserted into an external capsule 300. The external capsule 300 comprises a hollow cylinder 310, the base 311 of which is closed, and a screw-on closure cap 320. On the inside of the cylinder 310, parallel to and at a distance from the base 311, there is a support shoulder 313, which is intended to act as an axial stop for the first planar base side on the fixing part 210 of the inserted ampoule 200. In this case, the support shoulder 313 comprises four webs which are offset through 90° in each case. The closure cap 320 points towards the stand part 220 of the ampoule 200. At most in the region of the clearance between the second planar base side on the stand part 220 and the closure cap 320, the ampoule 200 can move on the axis M and otherwise lies in a stable position in the external capsule 300 in the event of vibrations.

The implant 1 is held by a holding element 100 with the screw 101 and the sleeve part 102. As has already been indicated, the externally threaded part 131 of the screw 101, which projects through the sleeve part 102, engages in the internally threaded bore 14 on the implant 1, while the mating shoulder 161 of the shoulder part 160 of the sleeve part 102 rests on the implant shoulder 11. The fixing part 110 of the holding element 100 is latched into the fixing part 210 of the ampoule 200, i.e. the cylindrical section 116 of the holding element 100 is clamped in the indent 212 in the ampoule 200 and is surrounded laterally by the two jaws 215,216. The two annular shoulders 115,117 of the holding element 100 bear against the fixing part 210 on both sides. In this way, the implant 1 is held in line with the centre axis M inside the ampoule 200 without coming into contact with the ampoule 200.

FIGS. 6A and 6B

The ratchet adapter 400 which can be attached to the extension 120 of the holding element 100,100' comprises the head part 401 and the shank attachment 402. The head part 401 has the outer profiling 430 which is complementary to a ratchet wrench and, on the end side, has an axial blind bore 431 for accommodating the pin of an unscrewing spanner. On the inside, the shank extension 402 has an internal polygon 410 which is complementary to the external polygon 121. On the outside, ahead of the internal polygon 410, there is a constriction 411 which reduces the clear diameter, so that a widened annular groove 412 is formed between the internal polygon 410 and the constriction 411. The annular groove 412 serves to accommodate a securing element which rests in the radial groove 123 on the extension 120 after the said securing element has overcome the constriction 411 when the ratchet adapter 400 is attached. As a result, the ratchet adapter 400 can, as it were, be latched onto the extension 120 and cannot become detached of its own accord.

FIG. 7

For handling purposes, an unscrewing spanner 700 is also provided, which serves to grip the external polygonal segment 170,170' on the sleeve part 102, 102' of the holding element 100,100'. At one end, the unscrewing spanner 700 is designed as an angled-off open-end wrench 701, and at the other end as a straight ring wrench 702. A guide pin 704 is situated on the flat side 703 in the region of the ring wrench 702. Whether the open-end wrench or the ring wrench 701,702 is employed depends on the spatial conditions and the preference of the user.

FIGS. 8A to 8J

The step-by-step handling of the ampoule 200 is explained in connection with the following sequence of figures, using, by way of example, an implant 1 and a holding element 100.

Step 1 (FIG. 8A): In the finished state, the ampoule 200 is positioned in the closed external capsule 300 comprising the cylinder 310 and the closure cap 320. The holding element 100 holds the implant 1 and, for its part, is fixed by the ampoule 200 in the indent 212. The entire contents of the external capsule 300 are sterile.

Step 2 (FIG. 8B): In order to open the external capsule 300, the closure cap 320 is removed from the cylinder 310.

Step 3 (FIG. 8C): The ampoule 200, with the implant 1 contained therein, is tipped out of the cylinder 310, which is now open, of the external capsule 300 onto a sterile surface.

Step 4 (FIG. 8D): The extension 120 with the external polygon 121 projects out of the ampoule 200. To attach screwing-in tools—namely a ratchet wrench or a dental handpiece—a ratchet adapter 400 or an adapter 450 for the dental handpiece—are kept ready. At one end, the adapter 450 has a standard dental coupling 451 and, opposite to the latter, a shank attachment 452, which is likewise intended for attachment to the extension 120 and has an internal structure which is analogous to the shank extension 402 of the ratchet adapter 400.

Step 5 (FIG. 8E): Depending on the screwing-in tool to be used, the ratchet adapter 400 or the adapter 450 for the dental handpiece 800 is attached to the extension 120 and the implant 1 is removed from the ampoule 200. The implant 1, which is suspended from the ratchet adapter 400 or from the adapter 450 and from the handpiece 800 by means of the holding element 100 is transferred to the location of use.

Step 6 (FIG. 8F): When using a ratchet spanner as the screwing-in instrument, the ratchet adapter 400 will first be taken hold of by hand and the implant 1 will be screwed to some extent into the bore KB which has been prepared in the bone K.

Step 7 (FIG. 8G): To screw the implant 1 in further, a ratchet wrench 600 and an unscrewing spanner 700 are placed upon the ratchet adapter 400. The guide pin 704 of the unscrewing spanner 700 engages in the blind bore 431. The implant 1 can also be screwed in by means of a motor-driven dental handpiece 800, as long as the associated adapter 450 has in advance been placed upon the holding element 100.

Step 8 (FIG. 8H): After screwing using a ratchet wrench 600 has been completed, the unscrewing spanner 700 is removed from the ratchet wrench 600.

Step 9 (FIG. 8I): Irrespective of whether the implant has been inserted using ratchet wrench 600 or by means of handpiece 800, in order to unscrew the holding element 100, i.e. firstly to unlock the sleeve part 102 from the implant head 10, the unscrewing spanner 700 is attached to the external polygonal segment 170. The open-end wrench 701 can be attached to the external polygonal segment 170 from the side. When attaching the ring wrench 702, which is carried out from above, it would first be necessary briefly to remove the screwing-in instrument 600,800, together with the associated adapters 400,450, from the extension 120 of the holding element 100. With the operating direction of the ratchet wrench 600 or handpiece 800 switched over and the unscrewing spanner 700 attached, the holding element 100 is unlocked from the implant 1. The unscrewing spanner 700 is then removed and the screw 101 is unscrewed until its externally threaded part 131 comes out of engagement with the internal screw thread 14 in the implant head 10.

Step 10 (FIG. 8J): Finally, the holding element 100 can be removed from the implant 1, which is now in situ.

Further design variations on the devices described above are possible. Express mention may be made of:

The holding element 100,100' can also be used for implants of different configuration. The important criterion is that the implants have an internally threaded bore 14 which is accessible from the outside in order for the externally threaded part 131 of the holding element 100 to be screwed in. Furthermore, the implants must have an implant shoulder 11 or a comparable surface for supporting the sleeve part 102.

Instead of the external polygon 121 on the screw 101, a different, external, non-rotationally symmetrical contour on the extension 120,120' is conceivable, as is an internal contour, if the tools to be attached were to have a complementary mandrel.

The jaws 215,216 on the ampoule 200 could generally be replaced by a clamping member.

For implants 1,1' with a conically widening implant head 10,10' rising beneath the implant shoulder 11,11', the following attachment for the holding element is provided as an alternative. In the case of the screw 101 which engages in the internally threaded bore 14,14' in the implant 1,1', the screw shaft 130, together with the externally threaded part 131 and cylindrical part 132, could be dispensed with. Sleeve part 102,102' and screw extension 120 would then form a single part. The temporary fixing of the holding element on the implant 1,1' is then realized by means of an elastic snap-in element at the bottom of the sleeve part 102,102' which, when pressed onto the implant shoulder 11,11', passes over the latter and then engages below it. This method of attaching the holding element is particularly expedient if the implant 1' has a polygonal segment 12' which projects above the implant shoulder 11', and/or if no internally threaded bore 14,14' is present. In this regard, reference is made to the attachment in accordance with the patent publication WO-A-97 28755 of the applicant.

What is claimed is:

1. In a holding element (100, 100') for an implant (1, 1') which is adapted to be inserted into bone (K) and has an implant head (10, 10'), an implant shoulder (11, 11') present thereon, and an internally threaded bore (14, 14'), which extends at least substantially in the axial direction, in which
    a) the holding element (100, 100') comprises a sleeve part (102, 102') and a rotatable screw (101) which projects through the sleeve part (102,102');
    b) the sleeve part (102, 102') has, at the bottom, a cylindrical shoulder part (160, 160') which terminates with a mating shoulder (161, 161') which is directed downwards and is complementary to the implant shoulder (11, 11')
    c) an upwardly directed external polygon segment (170, 170') extends above the shoulder part (160, 160');
    d) an axial bore (162, 162') allowing the passage of the shaft (130) of the screw (101) extends through the sleeve part (102, 102');
    e) an external threaded part (131) of the screw shaft (130) is adapted to engage in the internally threaded bore (14, 14') in the implant (1, 1');
    f) the screw (101) has an extension (120), which projects above the sleeve part (102, 102') and has a non-rotationally symmetrical contour (121), for the attachment of a tool; the improvement wherein
    g) the holding element (100, 100') is screwed to the implant (1, 1') already during the production of said implant (1, 1') and is utilized with said implant (1, 1') during further implant production phases, up to and including implantation; and
    h) a fixing part (110) is provided between the contour (121) and the sleeve part (102, 102'), which fixing part (110) serves for the attachment of a manipulation member in a device for operating, transportation, storage purposes and for retention inside an ampoule (200).

2. The holding element (100, 100') according to claim 1, wherein:
    a) an internally threaded section (163, 163'), which is complementary to the externally threaded part (131) of the screw shaft (130), is present in the axial bore (162, 162'); and
    b) above the externally threaded part (131) situated at the free end, the screw shaft (130) has a cylindrical part (132) which is slidable within the internally threaded section (163, 163'), so that the screw (101) which has been screwed into the sleeve part (102, 102') is movable axially to a limited extent.

3. The holding element (100, 100') according to claim 1 or 2, wherein:
    a) the fixing part (110) is formed by two collars (114, 118) which are spaced apart from one another and a cylindrical section (116) which lies between these two collars (114, 118) and has a reduced diameter in comparison with the collars (114, 118); such that
    b) an annular shoulder (115, 117) is formed at each of the transitions from the cylindrical section (116) to each of the collars (114, 118);
    c) the non-rotationally symmetrical contour (121) on the extension (120) of the screw (101) is an external polygon (121);
    d) a radial groove (123) for accommodating a securing element is provided between the external polygon (121) and the adjoining collar (118); and
    e) the collar (114) which faces towards the sleeve part (102, 102') has a conical shoulder (113) which comes to bear against a complementary support shoulder (171, 171') on the sleeve part (102, 102').

4. An ampoule (200) for transporting, storing and providing an implant (1, 1') directly before its insertion into the bone (K), which ampoule (200) has an outer cylindrical casing (230) and is insertable into an external capsule (300), the ampoule (200) comprising:
    a) a fixing part (210), into which the implant (1, 1') is insertable indirectly; and
    b) a lateral, large-area cutout (231) in the casing (230), through which cutout (231) the implant (1, 1'), which is held inside the ampoule (200), is removable.

5. The ampoule (200) according to claim 4, wherein:
    a) the fixing part (210) forms a planar base side of the cylindrical ampoule (200); and
    b) a laterally open indent (212), for the indirect clamping accommodation of the implant (1, 1'), is situated in the fixing part (210), which indent (212) faces in the same direction as the cutout (231).

6. The ampoule (200) according to claim 4 or 5, wherein the indent (212) has:

a) outwardly facing rounded sections (218);

b) a constriction (213), behind which the indent (212) widens again, in the region of a theoretical centre axis (M) of the ampoule (200); and c) an expansion groove (217), which extends the indent (212) toward the cylindrical casing (230).

7. The ampoule (200) according to claim 4 or 5, wherein:

a) a stand part (220), for standing the ampoule (200) vertically, lies opposite the fixing part (210), which is situated at one end of the ampoule (200), at the other end of the ampoule (200); and b) the cutout (231) terminates before the stand part (220), such that the casing (230) forms a radially continuous tubular section (221).

8. The ampoule (200) according to claim 4, wherein:

a) owing to an asymmetric distribution of material, the centre of gravity of the ampoule (200) lies outside a theoretical centre axis (M) of the ampoule (200), in order rapidly to decelerate a rolling movement of the ampoule (200); and b) two beads (233), which extend axially on either side of the cutout (231) and serve as an additional protection against the ampoule (200) rolling away, are provided outside the cylindrical casing (230).

9. The ampoule (200) according to claim 4, wherein said ampoule (200) is sized and shaped to receive an implant (1, 1') which is adapted to be inserted into bone (K) and which has an implant head (10, 10'), an implant shoulder (11, 11') present thereon, and an internally threaded bore (14, 14'), which extends at least substantially in the axial direction, in which a) a holding element (100, 100') is provided, which comprises a sleeve part (102, 102') and a rotatable screw (101) which projects through the sleeve part (102, 102');

b) the sleeve part (102, 102') has, at the bottom, a cylindrical shoulder part (160, 160') which ends with a mating shoulder (161, 161') which is directed downwards and is complementary to the implant shoulder (11, 11');

c) an upwardly directed an external polygon segment (170, 170') extends above the shoulder part (160, 160');

d) an axial bore (162, 162') allowing the passage of the shaft (130) of the screw (101) extends through the sleeve part (102, 102');

e) an external threaded part (131) of the screw shaft (130) is adapted to engage in the internally threaded bore (14, 14') in the implant (1, 1');

f) the screw (101) has an extension (120), which projects above the sleeve part (102, 102') and has a non-rotationally symmetrical contour (121), for the attachment of a tool; and wherein g) a fixing part (110), which projects above the sleeve part (200, 200') and serves for retaining purposes inside the ampoule (200), is provided beneath the contour (121);

h) the fixing part (110) of the holding element (100, 100') is adapted to be latched into the fixing part (210) of the ampoule (200), so that i) the holding element (100, 100'), which has been fixed in the ampoule (200), holds the implant (1, 1'), which is screwed to the holding element (100, 100'), inside the ampoule (200) and in line with a theoretical centre axis (M) of the ampoule (200).

10. The ampoule (200) according to claim 9, wherein:

a) the fixing part (110) of the holding element (100, 100') comprises two collars (114, 118), which are spaced apart from one another, and a cylindrical section (116) which lies between the collars (114, 118) and is of reduced diameter in comparison with the collars (114, 118);

b) an annular shoulder (115, 117) is formed at each of the transitions from the cylindrical section (116) to the collars (114, 118); and c) in the completed arrangement, with the implant (1, 1') inserted into the ampoule (200), the cylindrical section (116) being clamped into the indent (212) in the fixing part (210) of the ampoule (200), each of the annular shoulders (115, 117), respectively, bears against one side of the fixing part (210) of the ampoule (200).

11. The ampoule (200) according to claim 4, wherein axial retention of the ampoule (200), which has been inserted into the external capsule (300), is achieved by means of a closure cap (320), which belongs to the external capsule (300), and a support shoulder (313), which is arranged inside the external capsule (300), in the region of the base (311) of said external capsule (300), and on which the end side of the fixing part (210) of the ampoule (200) is supported.

12. The ampoule (200) according to claim 4, wherein:

a) the fixing part (210) forms a planar base side of the cylindrical ampoule (200); and b) a laterally open indent (212), for the direct clamping accommodation of the implant (1, 1'), is situated in the fixing part (21), which indent (212) faces in the same direction as the cutout (231).

13. An ampoule (200) for transporting, storing and providing an implant (1, 1') directly before its insertion into the bone (K), which ampoule (200) has an outer casing (230) and is insertable into an external capsule (300), the ampoule (200) comprising:

a) a fixing part (210), into which the implant (1,1') is insertable directly; and b) a lateral, large-area cutout (231) in the casing (230), through which cutout (231) the implant (1, 1'), which is held inside the ampoule (200) is removable.

* * * * *